(12) United States Patent
Baek et al.

(10) Patent No.: US 8,139,210 B2
(45) Date of Patent: Mar. 20, 2012

(54) REAL-TIME MONITORING APPARATUS FOR BIOCHEMICAL REACTION

(75) Inventors: Jong-Soo Baek, Daejeon (KR);
Dong-Yeon Cho, Sungnam-si (KR);
Hanee Park, Daejeon (KR); Han-Oh Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 771 days.

(21) Appl. No.: 10/551,784

(22) PCT Filed: Apr. 3, 2004

(86) PCT No.: PCT/KR2004/000785
§ 371 (c)(1),
(2), (4) Date: Oct. 3, 2005

(87) PCT Pub. No.: WO2004/088291
PCT Pub. Date: Oct. 14, 2004

(65) Prior Publication Data
US 2006/0145098 A1    Jul. 6, 2006

(30) Foreign Application Priority Data
Apr. 3, 2003  (KR) .................. 10-2003-0021145

(51) Int. Cl.
*G01J 3/00* (2006.01)
(52) U.S. Cl. ........... 356/300; 356/22; 356/73; 356/460; 422/68.1; 422/82.05; 422/82.11; 385/12
(58) Field of Classification Search ............ 422/68, 422/82.05–82.11; 356/22, 73, 300, 460; 385/12; 372/45
See application file for complete search history.

(56) References Cited

U.S. PATENT DOCUMENTS

| | | | |
|---|---|---|---|
| 4,076,420 A * | 2/1978 | De Maeyer et al. ............ 356/73 |
| 4,213,703 A | 7/1980 | Haunold et al. | |
| 4,689,797 A * | 8/1987 | Olshansky ................. 372/45.01 |
| 5,674,000 A | 10/1997 | Kalley | |
| 6,272,269 B1 | 8/2001 | Naum | |
| 6,396,581 B1 | 5/2002 | Hayashi et al. | |
| 2003/0002038 A1* | 1/2003 | Mawatari ..................... 356/300 |

FOREIGN PATENT DOCUMENTS

| | | |
|---|---|---|
| JP | 06-250137 A | 9/1994 |
| JP | 09-288237 A | 11/1997 |
| JP | 10-221242 A | 8/1998 |

(Continued)

OTHER PUBLICATIONS

Hessling, et al., "Fluorescence measurements on nanotiter plates", Review of Scientific Instruments, May 2000, vol. 71, No. 5, (p. 2201-2205).

*Primary Examiner* — In Suk Bullock
*Assistant Examiner* — Robert Eom
(74) *Attorney, Agent, or Firm* — The Nath Law Group; Jerald L. Meyer; Jiaxiao Zhang

(57) ABSTRACT

The present invention relates to an apparatus for real-time monitoring chemical reaction between various biomaterials. More particularly, the present invention directed to a real-time monitoring apparatus for biochemical reaction, which comprises parabolic mirror and/or an optical waveguide tube for effective irradiation of light over the whole plate with uniform intensity.

8 Claims, 4 Drawing Sheets

FOREIGN PATENT DOCUMENTS

| | | |
|---|---|---|
| JP | 2000088752 | 3/2000 |
| JP | 2000-149607 A | 5/2000 |
| JP | 2000214090 | 8/2000 |
| JP | 2001-100314 A | 4/2001 |
| WO | WO 96/09542 A1 | 3/1996 |
| WO | 99/64846 | 12/1999 |
| WO | 02/063300 A1 | 8/2002 |

* cited by examiner

REAL-TIME MONITORING APPARATUS FOR BIOCHEMICAL REACTION

TECHNICAL FIELDS

The present invention relates to an apparatus for real-time monitoring chemical reaction between various biomaterials. More particularly, the present invention is directed to a real-time monitoring apparatus for biochemical reaction, which comprises a temperature control block system comprising a thermoelectric element, capable of supplying heat into a reaction tube, a heat transmission block which transmit the heat to the reaction tubes; a light irradiation source part comprising a lamp which irradiates light with uniform intensity to sample contained in the reaction tube, and optical waveguide; and optical system comprising a light receiving part for receiving fluorescence irradiated from the sample by the light emitted from the light irradiation source.

BACKGROUND ART

The present invention relates to an apparatus for real-time monitoring chemical reaction between various biomaterials. More particularly, the present invention is directed to a real-time monitoring apparatus for biochemical reaction, which comprises a temperature control block system comprising a thermoelectric element, capable of supplying heat into a reaction tube, a heat transmission block which transmit the heat to the reaction tube; a light irradiation source part comprising a lamp which irradiates light with uniform intensity on sample contained in the reaction tube, and optical waveguide; and optical system comprising a light receiving part for receiving fluorescence irradiated from the sample by the light emitted from the light irradiation source.

Recently, the research and development for chemical microprocessor have been performed actively, which can carry out pretreatment of sample, reaction, separation, detection and etc., within a single chip, so called lab-on-a-chip. The lab-on-a-chip composed from glass, silicon or plastic material and manufactured through the lithography technology which has been employed for semiconductor chip, mounts micro-sized device for analyzing samples rapidly and sensitively.

The above all procedures required for the analysis of sample, i.e., pretreatment, reaction, separation, detection and etc., can be performed continuously. In addition, by using the chip the time needed for the sample analysis can be reduced to second or minute level and also the amount of sample can be reduced to micro-liter level and the size of apparatus on which the chip is mounted can also be miniaturized. The lab-on-a-chip technology is based on the capillary electrophoresis developed by Harrison in early 1990s, and had been started to be known to the public by the fact that a small size lab. Device for the capillary electrophoresis analysis can be integrated into a single chip.

Meanwhile, recently, so called real-time PCR technology which can check rapidly the progress of every cycle of amplification reaction by detection of fluorescence from reaction tubes, without using the separation step in gel phase. The conventional apparatus employed for this real-time PCR technology may be manufactured by coming the thermal cycler for PCR and the fluorometer for detection of products.

The conventional real-time PCR apparatus is composed of the thermoelectric element, the heat transmitting block which transmit heat into reaction tubes which contains sample, the light irradiation source which irradiate light into sample contained in the reaction tube, and the light receiving part which accept the fluorescence generated from the sample.

By using the conventional real-time PCR apparatus, the progress of PCR can be checked in real-time by measuring the intensity of fluorescence generated from sample upon completion of each cycle by the operation of the thermoelectric element for cooling and heating repeatedly to carry out the reaction of biochemical sample contained in the tube.

In the conventional real-time PCR apparatus, in general, a halogen lamp and a metallic halide lamp have been employed as a light irradiation source. In this conventional apparatus, a selective transmission filter(9) transmit selectively the light with preferred wavelength from the light radiated from the lamp(5) and then, the light thus selected irradiated into the sample contained in the tubes via a reflection mirror(18) and through a condensing lens(17).

Then, the sample contained in the tubes generate fluorescence by irradiation of light thus selected. The fluorescence thus generated, is reflected by reflection mirror(18) and focused through condensing lens(17). The fluorescence thus focused from each tubes is imaged on a light receiving element of the light receiving part to indicate and record the progress of reaction, continuously.

By the way, the light intensity generated from the light radiation lamp of the conventional apparatus, is differentiated depends on the positions, i.e., the center or the edges of the facet of light beam. Consequently, the light intensity generally varied with gaussian curve along with central axis of the facet of light beam and maintain this distribution even through the condensing lens.

This difference of brightness of light between the center and the edges of the facet of light beam, may cause a problem that the accurate data cannot be obtained since the fluorescence response from the sample positioned at the edges is weak. Various study and development have been tried to obviate this problem of the prior art. However, the technology which can overcome the above mentioned problem has not yet been suggested up to now. That is, a technology which can irradiate light with uniform intensity on the whole area of tube plate enlarged day by day, has not known in this field.

For the above reason, there is a critical limitation for enlarging the number of the tubes which can be monitored simultaneously. Therefore, the primary object of the present invention is to provide an apparatus for real-time monitoring the progress of biochemical reaction, which have technical part to irradiate light with uniform intensity over the whole area of the tube plate which is enlarged than that of prior art.

In addition, as depicted in FIG. 5, the reaction tube plate of prior art is in general rectangular shape. However the conventional light radiation system composed of a lamp and a lens, emits plane wave beam of which facet has round shape. Thus, some edge part of light beam should be eliminated to be fitted with the rectangular shaped tube plate. This problem lowers the efficiency of the source due to eliminated pat of light beam.

Various studies to obviate this problem of the low efficiency of light source have been suggested. However, any appropriate tools which can be adapted to a laboratory device integrated compactly, have not yet been developed.

Therefore, the present inventors had conceived that the sensitivity of the monitoring apparatus can be improved by strengthening the intensity of light by providing the light beam through waveguide which has a similar facet shape as that of the tube plate. Thus, another object of the claimed subject matter is to provide a real time monitoring apparatus for biochemical reaction which can irradiate light with uniform intensity over the whole area of the reaction tube plate, even over the whole area of the reaction tube plate enlarged than that of prior art, by irradiating light beam through a light irradiation part via a mirror.

BRIEF DESCRIPTION OF THE DRAWINGS

The above objects and other advantages of the present invention will become more apparent by describing in detail a preferred embodiment thereof with reference to the attached drawings, in which:

FIG. 3a shows a tube plate and FIG. 3b shows the light intensity distribution in X direction and in Y direction.

FIG. 4a shows a waveguide. FIG. 4b shows the distribution curve of the light intensity. FIG. 4c shows a schematic diagram of total internal refraction.

BRIEF DESCRIPTION OF THE DRAWINGS MARK

Figure 1:
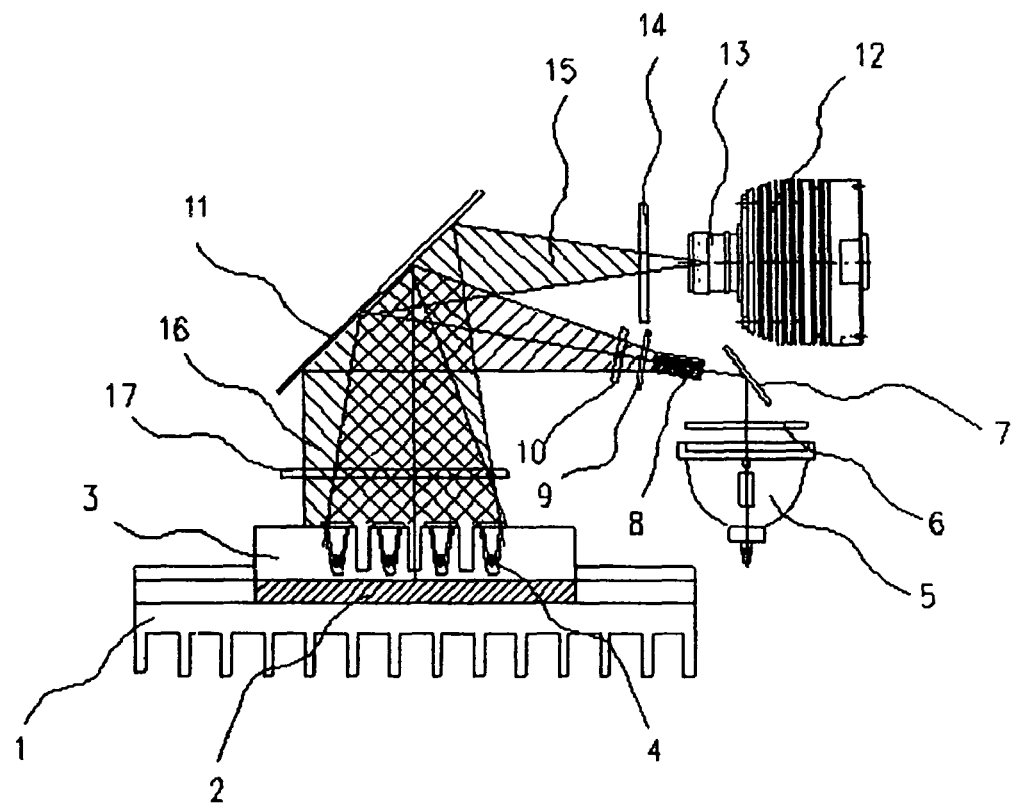
FIG. 1 is a schematic diagram of a real-time monitoring apparatus of the present invention for checking the process of biochemical reaction between various biological samples.
Figure 2:
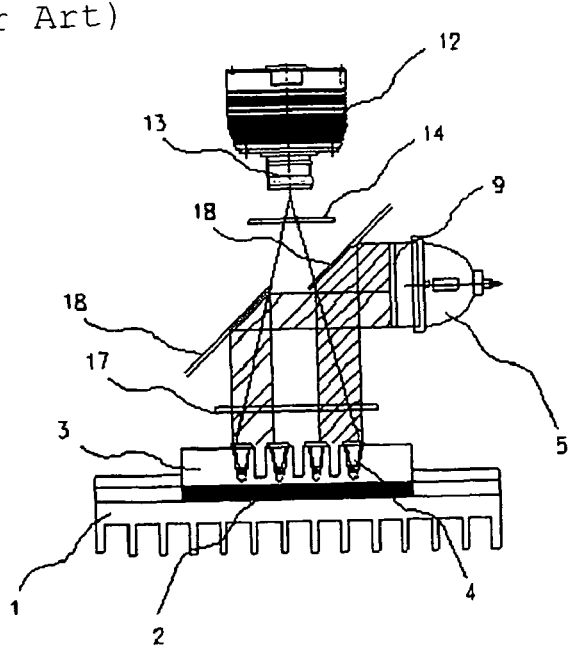
FIG. 2 is a schematic diagram of an apparatus of prior art for real-time monitoring of the progress of biochemical reaction.

1: heat sink plate
2: thermoelectric element
3: heat transmission block
4: reaction tube
5: lamp
6: Infra-Red cutting filter
7: reflective mirror 1
8: optical waveguide
9: selective transmission filter 1
10: focusing lens 1
11: reflective mirror 2
12: light received element
13: focusing lens 2
14: selective transmission filter 2
17: condensing lens
18: reflective mirror 3
25: incident light
26: the emitting light
28: distribution of the light intensity
33: condensing lens 2
34: tube plate
36: focusing lens 3
38: condensing lens 3
40: lamp with ellipsoidal mirror
41: lamp with parabolic mirror

DISCLOSURE OF THE INVENTION

The object of the present invention it to provide a real-time monitoring apparatus for biochemical reaction comprising: a temperature control block comprising a thermoelectric element(2) capable of supplying the heat into a reaction tube(4) and a heat transmission block(3) which transmit the heat to the reaction tube(4) containing a sample; a light irradiation source part comprising a lamp(5) which irradiates the light with uniform intensity of a sample contained in the reaction tube, a Infra-Red cutting filter(6) cutting Infra-Red from the lamp, an optical waveguide(8) and a first focusing lens(10) for obtaining uniform light beam of the light from the lamp in a wide area, a selective transmission filter 1(9) for transmitting light selectively to monitor a reaction progress selectively, a second reflective mirror(11), and first condensing lens(17); an optical system comprising a light receiving part (12, 13 and 14) for receiving fluorescence(15) generated by the light emitted from the light irradiation source.

Furthermore, another object of the present invention is to provide a real-time monitoring apparatus for biochemical reaction which has a ellipsoidal mirror to get an uniform light intensity distribution.

The light from the light radiation lamp (5) is focused into the light waveguide (8). The light in the light waveguide is propagated in a manner of total internal reflection. The light beam at the end of the light waveguide (8) become a uniform 2-dimensional light source and are focused on the samples contained in the reaction tubes (4) through the first condensing lens (10). By using the uniform light beam (31), there reaction progress may be more easily measured over the whole range of the reaction tubes.

Therefore, an apparatus capable of checking the progress of reaction more efficiently may be provided due to the reduced variation of radiation light intensity in each reaction tube by irradiating the light with uniform intensity over broader reaction tube area. The apparatus enables to process uniform reaction information while reacting various samples simultaneously in the reaction tubes.

Still another object of the present invention is to provide a real-time monitoring apparatus for biochemical reaction with improved reaction monitoring sensitivity. In the improved apparatus of the present invention, the usage efficiency of light source is improved by increasing the amount of light irradiated into the reaction tubes, as the result of minimizing the loss of the light source in prior art by irradiating rectangular light beam(37) adjusted to the aspect ratio of the rectangular reaction tube plate using a light waveguide(8).

The present invention relates to a measuring and monitoring apparatus for reaction progress in real-time while reacting various samples. More particularly, the present invention directed to a real-time monitoring apparatus for biochemical reaction comprising: a temperature control block comprising a thermoelectric element capable of supplying heat into reaction tubes and a heat transmission block for transmitting heat to the reaction tubes containing samples; a light irradiation source comprising a lamp which irradiates light with uniform intensity on the samples contained in the reaction tubes, a condensing lens and an optical waveguide; an optical system comprising a light receiving part for receiving fluorescence from the samples contained in the reaction tubes generated by the light irradiated from the light irradiation source.

The temperature control block of the present invention is comprised of thermoelectric element(2) for repeating cooling and heating cycles and heat transmission block(3) for transmitting heat to reaction tubes containing samples. Moreover, a radiating plate(1) may be additionally provided for increasing the efficiency of the thermoelectric element. When the cooling and heating process is carried out repeatedly by the temperature control block, the amount of biological samples in the reaction tubes in terms of a genetic amplification reaction will be gradually amplified to $2^n$ (n: the number of repeating cycle).

In the real-time monitoring apparatus for biochemical reaction of the present invention, the optical system comprised of a light irradiation source and a light receiving part for measuring the amplified reaction progress in real-time is placed on a temperature control block.

The light irradiation source of the present invention comprises a lamp(5) which irradiates light to a sample contained in reaction tubes, a Infra-Red cutting filter(6) intercepting the light from the lamp, an optical waveguide(8) and a first focusing lens (10) for obtaining uniform light beam of the light from the lamp in a wide area, a selective transmission filter 1(9) for transmitting light of specific wavelength selectively to monitor a reaction progress in the tube, condensing lens 1(17) for receiving the fluorescence(15) by the radiation light (16) and a second reflective mirror(11) which alters light path.

In the prior art, it is a fundamental problem that light intensity in the center of a reaction tube plate and light intensity(32) at the edges of the reaction tube plate are different each other. The present invention employs an optical waveguide(8) placed in front of the light source to reduce of the difference in light intensity between the center and the edges of the tube plate and solves the problem of the prior art.

The waveguide(8) is designed to irradiate the light beam from the light source uniformly over a wider range. The light beam from the light source experience a total internal reflection due to the refractive indexes between a propagating medium(n2) in the waveguide(8) and surrounding air(n1). The light beam entered into the waveguide(8) forms a uniform plane wave light source at the light outlet(27) thereof.

Generally, in the lamp or lens-type optical system, light intensity is more densely distributed in the center and less densely distributed at the edges. The light intensity at the edges is merely about 50-60% of that in the center. Due to the difference in light intensity, samples placed in the center shows a higher sensitivity and reaction level than the samples placed at the edges by the different amount of light intensity there between.

In prior art to solve the above problem, analysis has been made by adjusting the measured light intensity to the light intensity at the edges. This brings the sensitivity of the whole apparatus degraded. In addition, in case of using a ultra-sensitivity light receiving element to overcome the degradation problem of sensitivity, the apparatus requires the increase in size and costs.

The present invention solves the prior art problem by forming a first reflecting mirror(7) of the radiation light source (5) as a ellipsoidal mirror. With this structure, light beam are focused at one point and are put into the optical waveguide(8) as many as possible. The optical waveguide(8) is designated to provide light intensity more uniformly over the broader cross-section of light beam. The waveguide(8) employs the difference in refractive indexes between the propagation medium(n2) and surrounding air (n1). Light beam where an incident angle(i) of the incident beam(29) has equal to or larger than a critical angle(c) experience total internal reflection(30) inside the waveguide(8). The incident beam(29) are emitted from the light outlet(27) through the waveguide(8) without loss in light intensity due to the light distribution. In this manner, a highly uniform 2-diemnsional light source is formed at the light outlet(27) of the waveguide(8).

Figure 4:
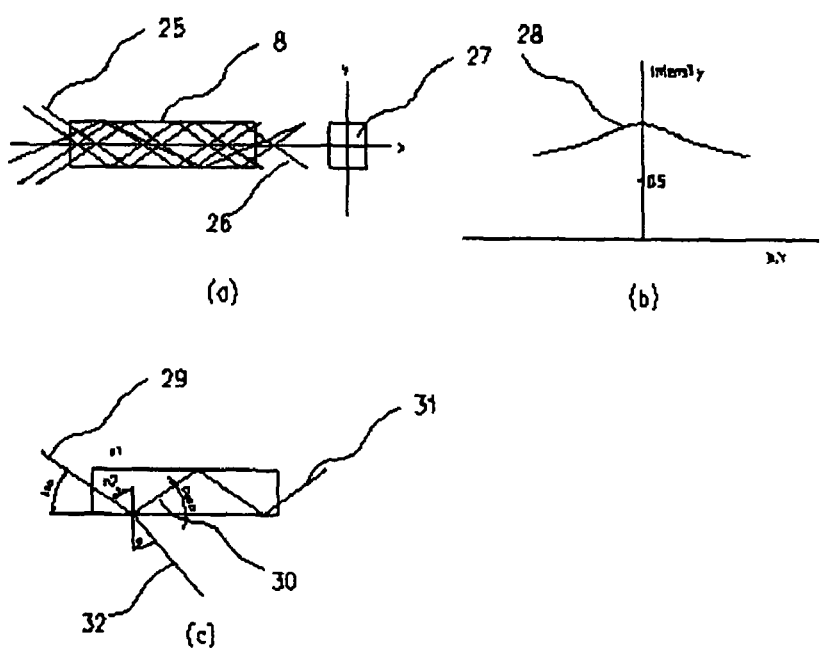
FIG. 4 is a schematic diagram of the optical waveguide for plane wave light in real-time monitoring apparatus of the present invention. Herein

In the present invention, the refractive index of the propagation medium in the optical waveguide(8) is preferably 1.35~2.0. The total internal reflection condition in a medium should satisfy that an incident angle(i) of incident light beam (29) is equal to or bigger than a critical angle(c). In FIG. 4, reference numeral 30 represents the reflected light beam, 26 for the emitting light beam, and 32 for the refracted light.

Under the condition of $n1\operatorname{Sin}(i)=n2\operatorname{Sin}(o)$, $n1=1.0$, $\sin(o)=1$ (n1: refractive index of air, o=90 degree)

$\sin(c)=n2$ (i (incident angle)>c (critical angle)

Figure 3:
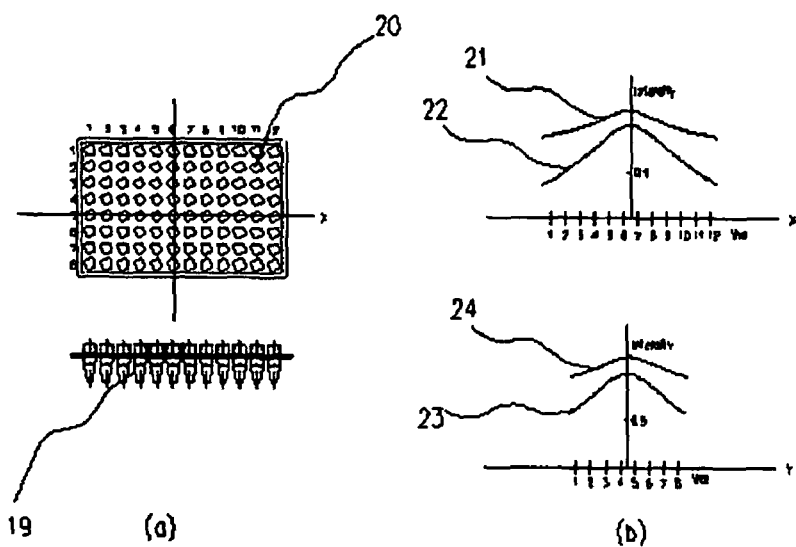
FIG. 3 represents the distribution of the luminosity on the tube plate of the real-time monitoring apparatus of the present invention. Herein

As shown in FIG. 3, a plane wave light source of the present invention with uniformly distributed intensity over the cross-section of light beam has more than 85% (21) of light intensity at the edges compared with the light intensity in the center of reaction tube plate(34) and enables to monitor the reaction progress more uniformly by achieving substantially improved light intensity uniformity compared with the prior art.

On the other hand, the typical reaction tube plate(34) used for proceeding the reactions of the various biological samples simultaneously is usually a rectangular shape, while the prior art optical radiation system comprising a lamp and a lens generates plane wave light beam with a round-type cross-section.

Figure 5:
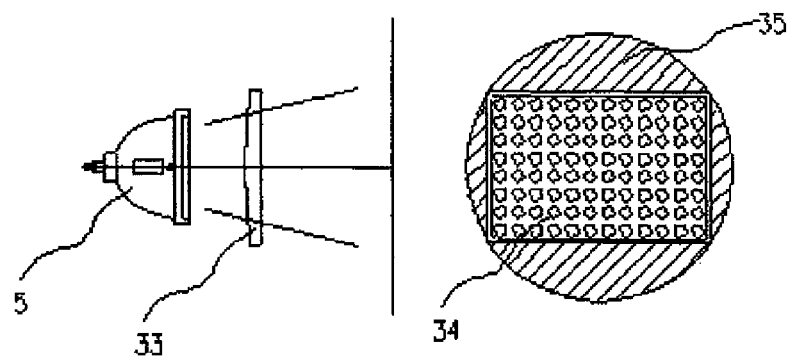
FIG. 5 is a schematic diagram of radiation system for plane wave light in the real-time monitoring apparatus of prior arts.

Therefore, as shown in FIG. 5, plane wave light beam with a round-type cross-section are adjusted to the shape of the rectangular reaction tube plate(34) and the remaining portions(35) unnecessary for the rectangular shape are removed. The removal of light beam(35) results to the removal of a portions of light beam from the light source lamp and causes graded efficiency of the light source. In FIG. 5, reference numeral 35 represents the removed light beam.

Figure 6:
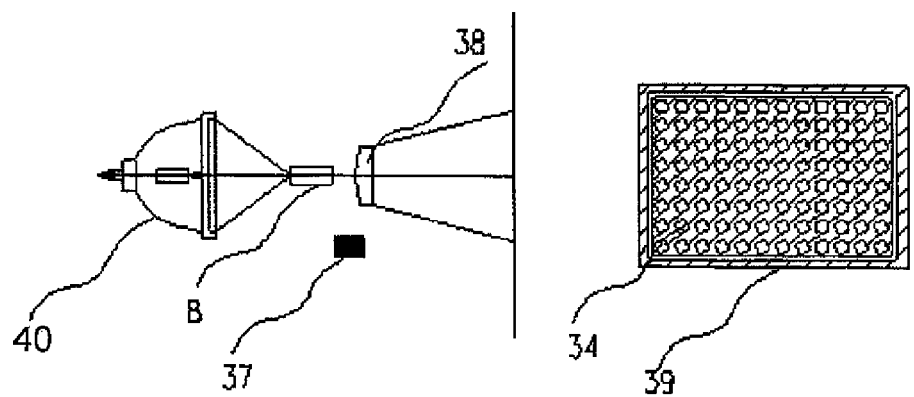
FIG. 6 is a schematic diagram of radiation system for plane wave light in real-time monitoring apparatus of the present invention.
Figure 7:
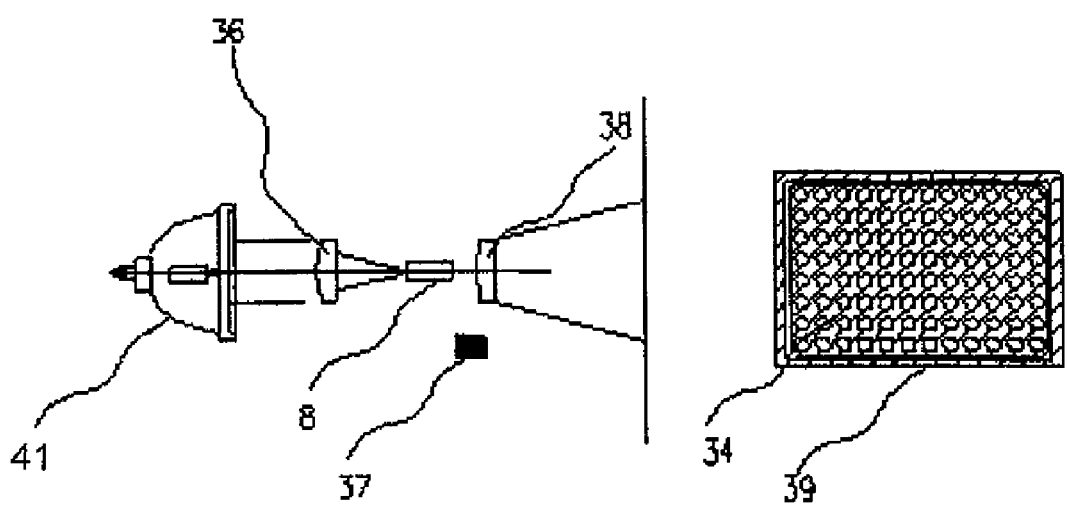
FIG. 7 is another schematic diagram of light radiation system for plane wave light in real-time monitoring apparatus of the present invention.

However, as shown in FIG. 6, the light waveguide(8) of the present invention has a shape of a rectangular cross-section (37) to be fitted with the aspect ratio of the rectangular plate (34) so that it is able to use the light from the lamp in it maximum efficiency because there are no light beam to be removed. As referenced by the reference numerals 21 and 24 in FIG. 3, the monitoring sensitivity of present invention is improved by increasing the light intensity irradiated on the plate to more than 20%. In FIG. 3, the reference numerals 21 and 24 represent the brightness distribution along the X-axis and Y-axis, respectively. Reference numerals 22 and 23 represent the brightness distribution along the X-axis and Y-axis, respectively, of prior art.

The radiation light controlled to a plane wave light source shape is irradiated on the samples contained in the reaction tubes(4) placed on the plate through a first focusing lens(10), a first selective transmission filter(9), a second reflecting mirror(11) and a first condensing lens. The nucleic acid samples in the reaction tubes are amplified per every cycle by the temperature block and fluorescence is generated from the amplified samples by the radiation light.

Meanwhile, the light receiving part of the present invention comprises a second focusing mirror(13) imaging fluorescence(15) from the samples contained in the reaction tubes(4) to the direction of an imaging element by the first condensing lens(17) and the second reflecting mirror(11); a light receiving element(12) for recoding the imaged figure by the second focusing lens(13) and a second selective transmission filter (14).

The fluorescence(15) generated from the samples is imaged on the light receiving element(12) by a second focusing lens(13) through the condensing lens 1(17), the reflecting mirror 2(11) and the second selective transmission filter (14). The images by fluorescence of each sample are transferred to a computer which analyzes the changing reaction progress per every cycle. Furthermore, it is possible to compare and analyze while per each sample by reacting various biochemical samples in the reaction tube plate described analyzing the reaction progress for each sample.

As described above, the real-time monitoring apparatus for biochemical reaction of the present invention, employs the lamp(S) with the ellipsoidal-type mirror and the optical waveguide(8), and there may be capable of monitoring the biological reaction progress with uniform sensitivity over the whole reaction plate area over the whole reaction plate(34).

Using the apparatus of the present invention with uniform light intensity, the present invention efficiently performs the comparative analysis of various samples while reacting the various samples simultaneously on one reaction tube plate by monitoring the reaction progress of the samples contained in the reaction tubes between the center and the edges of the reaction tube plate, more accurately.

According to the prior art, the reaction progress of the samples contained in the reaction tubes is equal to in the center and at the edges while there are limitations when performing a comparative analysis of the reaction progress for the samples due to the difference in light intensity of measured fluorescence. The present invention overcomes the limitation of prior art. Therefore, the real-time monitoring apparatus for biochemical reaction of the present invention is able to provide an appropriate apparatus for performing a comparative analysis of the reaction progress of the various samples by minimizing variation of light detection sensitivity during the reaction in the reaction tube plate.

Moreover, the present invention provides a profile of the light beam from the light source which is adjusted to a rectangular shape to be fitted with the aspect ration of the rectangular shape of the reaction tube plate. This adjusted profile of the present invention excludes the necessity of removing some portions of the light beam in the prior art and enables to use the light beam from the light source lamp at the maximum efficiency which improves energy efficiency of the present apparatus accordingly.

What is claimed is:

1. A real-time monitoring apparatus for biochemical reaction, comprising:
    a thermoelectric element capable of supplying heat into reaction tubes;
    a heat transmission block which transmits the heat to the reaction tubes;
    a tube plate capable of holding a sample;
    a lamp for irradiating to a sample contained in at least one of the reaction tubes in the tube plate;
    at least one reflective mirror;
    an optical waveguide positioned in front of the lamp which has an open structure in cooperation with said reflective mirror, said optical waveguide having a configuration that alters a light path passing through at least one end of the optical waveguide and provides a uniform intensity of light;
    an infra-red cutting filter filtering light transmitted through a light path that comprises said infra-red cutting filter, said reflective mirror and the optical waveguide and said infra-red cutting filter cutting infra-red from the lamp and a selective transmission filter for transmitting light selectively to monitor a reaction progress;
    said light transmitted through a light path illuminating the sample with a uniform light intensity distribution as provided by the uniform intensity of light from the optical waveguide, the optical waveguide reducing of the difference in light intensity between the center and the edges of the tube plate;
    a condensing lens positioned outside of a portion of a light path comprising said reflective mirror, the optical waveguide and the infra-red cutting filter;
    an optical system comprising a receiving part for receiving fluorescence transmitted through a second focusing lens, using a light receiving element capable of receiving the fluorescence, the fluorescence irradiated from the sample by light emitted from a light irradiation source as transmitted through a light path comprising the optical waveguide, the selective transmission filter and a first focusing lens; and
    said components arranged so that light will travel through optical components of the real time monitoring apparatus in the order of the lamp, the infra-red cutting filter, the optical waveguide, the selective transmission filter, the first focusing lens through the sample and the light receiving element.

2. The real-time monitoring apparatus according to claim 1, wherein the lamp includes an ellipsoidal reflecting mirror or a parabolic mirror.

3. The real-time monitoring apparatus according to claim 1, wherein the refractive index of medium of the optical waveguide is 1.35~2.0.

4. The real-time monitoring apparatus according to claim 1, wherein:
    the reaction tube plate has a rectangular layout; and
    the optical waveguide has a rectangular shape, thereby minimizing the loss of the light emitted from the light irradiation source by irradiating the light transmitted through the light path in a rectangular light beam adjusted to an aspect ratio of the reaction tube plate using the optical waveguide.

5. The real-time monitoring apparatus according to claim 1, wherein the cross-section of the optical waveguide has a round shape.

6. The real-time monitoring apparatus according to claim 1, further comprising two or more reflective mirrors positioned to alter light path after transmission from the light irradiation source.

7. The real-time monitoring apparatus according to claim 2, wherein the lamp including a parabolic mirror further comprises the first focusing lens.

8. A real-time monitoring apparatus for biochemical reaction, comprising:
    a thermoelectric element capable of supplying heat into reaction tubes;
    a heat transmission block which transmits the heat to the reaction tubes;
    a tube plate capable of holding a sample;
    a lamp for irradiating to a sample contained in at least one of the reaction tubes in the tube plate;
    at least one reflective mirror;
    an optical waveguide positioned in front of the lamp which has an open structure in cooperation with said reflective mirror, said optical waveguide having a configuration that alters a light path passing through at least one end of the optical waveguide and provides a uniform intensity of light;
    an infra-red cutting filter filtering light transmitted through a light path that comprises said infra-red cutting filter, said reflective mirror and the optical waveguide and said infra-red cutting filter cutting infra-red from the lamp and a selective transmission filter for transmitting light selectively to monitor a reaction progress;
    said light transmitted through a light path illuminating the sample with a uniform light intensity distribution as provided by the uniform intensity of light from the optical waveguide, the optical waveguide reducing of the difference in light intensity between the center and the edges of the tube plate;

a condensing lens positioned outside of a portion of a light path comprising said reflective mirror, the optical waveguide and the infra-red cutting filter;

an optical system comprising a receiving part for receiving fluorescence transmitted through a second focusing lens, using a light receiving element capable of receiving the fluorescence, the fluorescence irradiated from the sample by light emitted from a light irradiation source as transmitted through a light path comprising the optical waveguide, the selective transmission filter and a first focusing lens; and said components arranged so that light will travel through optical components of the real time monitoring apparatus in the order of the lamp, the infra-red cutting filter, the selective transmission filter, the optical waveguide, the first focusing lens through the sample and the light receiving element.

* * * * *